United States Patent
Song et al.

(10) Patent No.: US 11,219,897 B2
(45) Date of Patent: Jan. 11, 2022

(54) DEVICE FOR SEPARATING OR ALIGNING FINE PARTICLES, AND METHOD FOR SEPARATING OR ALIGNING FINE PARTICLES USING SAME

(71) Applicant: CURIOSIS Co., Ltd., Seoul (KR)

(72) Inventors: Seung Jeong Song, Yongin-si (KR); Ho Young Yun, Uijeongbu-si (KR)

(73) Assignee: CURIOSIS CO., LTD., Seoul (KR)

( * ) Notice: Subject to any disclaimer, the term of this patent is extended or adjusted under 35 U.S.C. 154(b) by 671 days.

(21) Appl. No.: 16/066,090

(22) PCT Filed: Dec. 30, 2016

(86) PCT No.: PCT/KR2016/015592
§ 371 (c)(1),
(2) Date: Jun. 26, 2018

(87) PCT Pub. No.: WO2017/116214
PCT Pub. Date: Jul. 6, 2017

(65) Prior Publication Data
US 2020/0269242 A1 Aug. 27, 2020

(30) Foreign Application Priority Data
Dec. 31, 2015 (KR) .................. 10-2015-0191430

(51) Int. Cl.
*B01L 3/00* (2006.01)
*G01N 33/49* (2006.01)

(52) U.S. Cl.
CPC ... *B01L 3/502746* (2013.01); *B01L 3/502753* (2013.01); *G01N 33/491* (2013.01)

(58) Field of Classification Search
None
See application file for complete search history.

(56) References Cited

U.S. PATENT DOCUMENTS

| | | | | |
|---|---|---|---|---|
| 5,234,813 A * | 8/1993 | McGeehan | ....... | B01L 3/502715 422/404 |
| 2006/0011480 A1* | 1/2006 | Sano | ............... | G01N 27/44704 204/601 |
| 2006/0063271 A1* | 3/2006 | Putnam | ........... | G01N 35/00732 436/174 |
| 2007/0059680 A1 | 3/2007 | Kapur et al. | | |
| 2014/0174994 A1* | 6/2014 | Bemate | ..................... | B03B 5/28 209/155 |
| 2014/0190903 A1 | 7/2014 | Huang | | |
| 2014/0341788 A1* | 11/2014 | Kim | ................... | B01L 3/502753 422/533 |
| 2015/0238963 A1* | 8/2015 | Han | ..................... | B01F 5/0606 435/30 |
| 2016/0121331 A1* | 5/2016 | Kapur | .................... | A61K 35/28 435/30 |
| 2016/0161378 A1* | 6/2016 | Kim | .................... | G01N 1/4077 422/527 |

FOREIGN PATENT DOCUMENTS

| | | |
|---|---|---|
| JP | 11-267593 | 10/1999 |
| JP | 2015-051430 | 3/2015 |
| KR | 10-2011-0005963 | 1/2011 |
| KR | 10-2014-0135159 | 11/2014 |
| WO | 2009-144928 | 12/2009 |
| WO | 2013-049860 | 4/2013 |

OTHER PUBLICATIONS

EPO, The extended European search report of EP 16882166.8 dated Apr. 18, 2019.
Byeongyeon Kim et al., "Deterministic Migration-Based Separation of White Blood Cells", Small, vol. 12, Issue 37, DOI: 10.1002/smll.201601652, Oct. 2016.

* cited by examiner

*Primary Examiner* — Ann Y Lam
(74) *Attorney, Agent, or Firm* — Lex IP Meister, PLLC

(57) ABSTRACT

Provided are a chip for separating or aligning fine particles, a device for separating or aligning fine particles including two or more chips for separating or aligning fine particles, and a method for separating or aligning fine particles using the chip for separating or aligning fine particles or the device for separating or aligning fine particles. The chip for separating or aligning fine particles includes: (i) a passage part in which a space where a fluid including fine particles which are capable of flowing is integrally formed and which has an inclined groove formed on one surface thereof; (ii) an inlet part which is positioned on one end of the passage part and into which the fluid is introduced; and (iii) a fine particle discharge part which is positioned on one side surface of the passage part, wherein one or more inclined grooves are formed to be inclined at an angle greater than 0° and less than 90° with respect to a line which is perpendicular to both side surfaces of the passage part.

28 Claims, 18 Drawing Sheets

DEVICE FOR SEPARATING OR ALIGNING FINE PARTICLES, AND METHOD FOR SEPARATING OR ALIGNING FINE PARTICLES USING SAME

CROSS-REFERENCE TO RELATED APPLICATION

This application claims priority to and the benefit of Korean Patent Application No. 10-2015-0191430 filed in the Korean Intellectual Property Office on Dec. 30, 2015, the entire contents of which are incorporated herein by reference.

TECHNICAL FIELD

The present disclosure relates to a device for separating and/or aligning fine particles and a method for separating and/or aligning the fine particles using the same. More specifically, the present disclosure relates to a device for more efficiently separating and/or aligning the fine particles by forming a certain pattern in the flow passage of fluid including the fine particles, and a method thereof.

BACKGROUND ART

Generally, for the purpose of research and development and diagnosis process of medical and biotechnological fields, a pretreatment process for extracting or removing specific substances is required in order to analyze a diagnostic factor such as a cell. For such process of extracting or removing specific substances, a separating method using centrifuge is widely used. However, since the separation process using centrifuge requires an expensive centrifuge device and is difficult to carry, thus limiting the conditions for use and making it impossible to continuously separate particles, there is a disadvantage that repetitive centrifugation process is required to process large samples.

Accordingly, recently, in order to overcome such disadvantages, a cell separating device based on a microfluidic technology such as an inertial fluid device or a dielectrophoretic device has been developed, but these cell separation devices have a disadvantage that they operate only under a specific condition such as a specific dilution ratio, or have varying efficiency depending on the flow rate of the fluid. For example, in the case of a dielectrophoretic device, the cell separation efficiency tends to decrease as the flow rate increases, and in the case of an inertial fluid device, the cell separation efficiency tends to decrease as the flow rate decreases. In addition, since the above methods use an external force such as an electric field or a magnetic field, a separate power source should be provided, and since the above methods use a slow flow rate, there is a problem in that the methods cannot separate a large amount of fine particles in a short time.

Accordingly, there has been a demand for a device for separating and/or aligning fine particles, which is capable of overcoming the disadvantage described above, that is, which is capable of separating fine particles from the fluid including the fine particles without using the external energy regardless of the flow rate, while ensuring convenience such as portability and so on, and fine particle separating performance, and a separating method using the same.

DISCLOSURE

Technical Problem

The present invention has been made in an effort to provide a device for separating and aligning the fine particles providing a technology of separating and/or aligning specific fine particles from a fluid sample to a desired direction more economically and conveniently based on a control of pattern shape.

An exemplary embodiment of the present invention provides a chip for separating or aligning fine particles, including: (i) a passage part in which a space where a fluid including fine particles which are capable of flowing is integrally formed and which has a groove formed on one surface thereof;

(ii) an inlet part which is positioned on one end of the passage part and into which the fluid is introduced; and (iii) a fine particle discharge part which is positioned on one side surface of the passage part.

In the chip for separating or aligning the fine particles, one or more grooves may be formed to be inclined at an angle greater than 0° and less than 90° with respect to a line which is perpendicular to both side surfaces, and the one side surface of the passage part on which the fine particle discharge part is positioned may be: a side surface of the passage part positioned in a perpendicular direction to the inclined direction; the other end of the passage part connected to the side surface of the passage part; or a corner at which the side surface and the other end are connected.

Yet another embodiment of the present invention provides a device for separating or aligning fine particles, including: two or more chips for separating or aligning fine particles described above. In the device for separating or aligning the fine particles, the two or more chips for separating or aligning fine particles may be arranged in parallel.

Yet another embodiment of the present invention provides a method for separating or aligning fine particle, including:

(1) injecting a fluid including fine particles into the chip for separating or aligning the fine particles or to the device for separating or aligning the fine particles; and (2) collecting fine particles discharged from a discharge part of the chip for separating or aligning the fine particles or a discharge part of the device for separating or aligning the fine particles.

Yet another embodiment of the present invention provides a kit for separating or aligning fine particle, including: the chip for separating or aligning the fine particles described above or the device for separating or aligning the fine particles described above; and a fluid supply part connected to an injection part of the chip for separating or aligning the fine particles, or to an injection part of the device for separating or aligning the fine particles.

According to an embodiment of the present invention, the chip for separating or aligning the fine particles, the device for separating or aligning the fine particles, the kit for separating or aligning the fine particles, or the method for separating or aligning the fine particles described above can be advantageously applied for separating leukocytes from blood, separating and/or purifying the proteins or peptides of antibodies, and so on, or aligning specific cells.

It is to be understood that the technical objectives to be achieved by the present disclosure are not limited to those mentioned above and other technical problems that are not mentioned will be apparent to those skilled in the art from the following description.

Technical Solution

The present disclosure proposes a chip for separating and/or aligning fine particles, which is capable of separating and/or aligning fine particles from a fluid more conveniently and rapidly and with high separating efficiency and/or accuracy, a device for separating and/or aligning fine particles including said chip for separating and/or aligning fine particles, and a method for separating and/or aligning fine particles using said chip or device for separating and/or aligning the fine particles.

One example provides a chip for separating or aligning fine particle, including:

(i) a passage part in which a space where a fluid including fine particles which are capable of flowing is integrally formed and which has a groove formed on one surface thereof;

(ii) an inlet part which is positioned on one end of the passage part and into which the fluid is introduced; and (iii) a fine particle discharge part which is positioned on one side surface of the passage part.

The groove is a structure (recessed groove) that forms a space in negative relief in an inner space of the passage part and it refers to a groove that is formed to be inclined with respect to both side surfaces or both ends of the passage part. In order to make it clear that the groove formed on one side surface of the passage part is formed to be inclined, the groove is referred herein as an 'inclined groove'. The one surface on which the inclined groove is formed may be one of the surfaces (lower surface and upper surface) of the chip except the inlet part (one end), the discharge part (the other end), and both side surfaces.

One or more, two or more, three or more, or four or more inclined grooves may be formed to be inclined at an angle greater than 0° and less than 90° with respect to a line which is perpendicular to both side surfaces of the passage part. More specifically, the inclined groove may include one or more, or two or more inclined grooves formed in the inclined direction, and/or one or more or two or more inclined grooves formed in a direction from the one end where the inlet part for the fluid is positioned, to the other end (i.e., in a main moving direction of the fluid in the passage part).

The passage part is a structure that includes the one or more inclined grooves that allow the entire area to be in fluid communication, thus allowing the fluid to pass through all areas of the passage part.

The one side surface on which the fine particle discharge part is positioned may be: a side surface of the passage part positioned in a direction perpendicular to the inclined direction (and to the main moving direction of the fluid) (and more specifically, a portion of the side surface opposite the inlet part, hereinafter the same); an end connected to the side surface (a portion of the other end with reference to the one end on which the inlet part is positioned; simply, 'other end'); or a corner at which the side surface and the other end are connected.

The 'fine particles' as used herein refer to the particles having a predetermined size and volume, and may have an average diameter of about 1000 um or less, about 500 um or less, about 100 um or less, about 50 um or less, about 30 um or less, about 20 um or less, about 15 um or less, or about 10 um less (Since the average diameter cannot be zero, the lower limit of the above numerical range may be selected from the numerical values exceeding 0).

The fine particles may be spherical, elliptical, amorphous, or the like, but not limited thereto. In one example, the fine particles may be one or more selected from the group consisting of cells including hematopoietic cells such as erythrocytes, leukocytes, or the like, cancer cells, stem cells, and normal cells, protein particles, beads to which proteins or peptides are attached, liposomes, micelles, or the like.

The fluid may be a fluid (e.g., suspension, dispersion, colloidal solution, etc.) including the fine particles described above. In one example, the fluid may be non-viscous fluid or may have a viscosity within a flowable range. For example, the fluid may be a fluid that is non-viscous or has a viscosity to a level similar to the viscosity of the blood, but not limited thereto. When the fluid includes two or more kinds of fine particles having different average diameters, the fine particles that can be separated and/or aligned by the technology for separating and/or aligning fine particles provided herein may be particles having the largest average diameter.

In one example, the fine particles to be separated may be leukocytes, and the fluid may be blood. In this case, the blood may be whole blood, or blood diluted 1 to 20 times by volume with respect to whole blood. In another example, the fine particles to be separated may be proteins (e.g., antibodies) or beads to which the proteins (or antibodies) are attached, and the fluid may be a suspension including the beads. When the fine particles to be separated are leukocytes and the fluid is blood, the chip for separating and/or aligning the fine particles or a device including the chip may be one provided for separating or removing leukocytes from the blood. When the fine particles to be separated are antibodies or beads to which antibodies are attached, the chip for separating and/or aligning the fine particles or a device including the chip may be used for antibody purification. When the fine particles to be separated and/or aligned are predetermined cells, the chip for separating and/or aligning the fine particles or a device including the chip may be used for separating and/or aligning the cells.

The chip for separating and/or aligning the fine particles may further include a fluid discharge part for separating the fluid from which the fine particles have been removed: on a side surface opposite to the fine particle discharge part, that is, on a side surface opposite to the one side surface on which the fine particle discharge part is positioned (more specifically, a portion of the side surface opposite to the inlet part, hereinafter the same); on the other end connected to the side surface; or on a corner at which the side surface and the other end are connected to each other.

In one example, when the fine particles to be separated are leukocytes and the fluid is blood, the leukocytes may be separated and/or aligned in the fine particle discharge part of the chip for separating and/or aligning the fine particles, and the blood from which leukocytes have been removed may be collected.

Hereinafter, the structure of the chip for separating and/or aligning fine particles will be described in more detail (see FIGS. 4A and 4B).

The space of the passage part where the fluid can flow may be a space that is closed except the inlet part (which may be formed as a separate space or may be an upper surface of the passage part (from which the flow of fluid starts)) and the discharge part and may be integrally formed to allow the fluid introduced from the inlet part to flow to the discharge part. The passage part may be an integrated structure in fluid communication that connects the inlet part with the discharge part, and may be a linear shape or a shape including one or more bending parts, but not limited thereto.

The inclined groove refers to a region that forms a space in negative relief (recessed groove) in the inner space of the passage part where the fluid flows. That is, either the upper plate or the lower plate (i.e., the surfaces except both ends and both side surfaces where the inlet part and the discharge part are positioned) of the passage part is a structure that partially has irregularities. The shape of the inclined groove is not limited. For example, the shape of the inclined groove may be polygons having a convex cross section in the horizontal or vertical direction (e.g., rectangular, square, rhombic, trapezoidal, triangular, etc.), concave polygons (e.g., star-shaped), circular, elliptical, or the like.

In the present disclosure, a region of the passage part where the inclined grooves are not formed, that is, the region between the inlet part and the inclined groove(s) closest to the inlet part, a region between one or more inclined grooves formed in the inclined direction, a region between one or more inclined grooves formed in a direction from the end with the inlet part to the other end, and a region including the region between the discharge part and the slope groove(s) closest to the discharge part may be referred to as a channel part.

The passage part having the inclined grooves formed therein has an inner space with a height (depth: h), in which the height may be a sum of the channel part height (depth: $h_c$) plus the height of the inclined grooves (when the inclined grooves are formed in the upper plate of the passage part), or plus the depth ($h_r$) of the inclined grooves (when the inclined grooves are formed in the lower plate of the passage part).

One or more, or two or more inclined grooves may be formed to be inclined at an angle greater than 0° and less than 90° (denoted by θ in FIG. 4A) with respect to an imaginary line (represented as B-B in FIGS. 4A and 4B) perpendicular to both side surfaces of the passage part, although the line may also be represented as a perpendicular line between the one end where the inlet part is positioned and the other end, when both side surfaces are curved or not parallel.

In FIG. 4A, C represents the main moving direction of the fluid, and D represents a direction perpendicular to the inclined direction in which the inclined groove is formed and to the main moving direction of the fluid, that is, D represents a direction in which the fine particles move (i.e., the direction where the fine particle discharge part is positioned).

FIG. 4B schematically shows a cross section in A-A direction at an angle θ with respect to B-B in FIG. 4A, which shows that an inner space having irregularities is formed.

The inclined angle of the inclined groove may be expressed with reference to an angle θ formed by a line perpendicular to both side surfaces of the passage part (or a line perpendicular between the one end where the inlet part is positioned and the other end) and a center line of the groove (i.e., center line in the longitudinal direction). Since the fine particles move and are separated and/or aligned in a direction perpendicular to the inclined surface of the inclined groove, the inclined angle of the inclined groove may be determined in consideration of the direction in which the fine particles are to be collected.

For example, with reference to an angle θ formed by a line perpendicular to both side surfaces of the passage part (or a line perpendicular between the one end where the inlet part is positioned and the other end) and a center line of the groove (i.e., center line in the longitudinal direction), the inclined angle of the inclined groove may be expressed as greater than 0° and less than 90°, greater than 0° and 80° or less, greater than 0° and 70° or less, greater than 0° and 60° or less, greater than 0° and 50° or less, greater than 0° and 45° or less, greater than 0° and 40° or less, greater than 0° and 35° or less, greater than 0° and 30° or less, greater than 0° and 25° or less, greater than 0° and 20° or less, greater than 0° and 15° or less, greater than 0° and 10° or less, greater than 0° and 5° or less, 5° to 90°, 5° to 80°, 5° to 70°, 5° to 60°, 5° to 50°, 5° to 45°, 5° to 40°, 5° to 35°, 5° to 30°, 5° to 25°, 5° to 20°, 5° to 15°, 5° to 10°, 10° to 90°, 10° to 80°, 10° to 70°, 10° to 60°, 10° to 50°, 10° to 45°, 10° to 40°, 10° to 35°, 10° to 30°, 10° to 25°, 10° to 20°, 10° to 15°, 15° to 90°, 15° to 80°, 15° to 70°, 15° to 60°, 15° to 50°, 15° to 45°, 15° to 40°, 15° to 35°, 15° to 30°, 15° to 25°, 15° to 20°, 20° to 90°, 20° to 80°, 20° to 70°, 20° to 60°, 20° to 50°, 20° to 45°, 20° to 40°, 20° to 35°, 20° to 30°, 20° to 25°, 25° to 90°, 25° to 80°, 25° to 70°, 25° to 60°, 25° to 50°, 25° to 45°, 25° to 40°, 25° to 35°, 25° to 30°, 30° to 90°, 30° to 80°, 30° to 70°, 30° to 60°, 30° to 50°, 30° to 45°, 30° to 40°, 30° to 35°, 35° to 90°, 35° to 80°, 35° to 70°, 35° to 60°, 35° to 50°, 35° to 45°, 35° to 40°, 40° to 90°, 40° to 80°, 40° to 70°, 40° to 60°, 40° to 50°, or 40° to 45°.

In the chip, one or more, two or more, three or more, or four or more inclined grooves may be formed to be inclined at an angle greater than 0° and less than 90° with respect to a line which is perpendicular to both side surfaces of the passage part More specifically, one or more or two or more inclined grooves may be formed in the inclined direction, and one or more or two or more inclined grooves may be formed in a direction from the one end where the inlet part is positioned toward the other end (i.e., in the main moving direction of the fluid, denoted by C in FIG. 4A).

The passage part is a structure that includes the one or more inclined grooves that allow the entire area to be in fluid communication, thus allowing the fluid to pass through all areas of the passage part.

The one or more inclined groove(s) as formed may not be parallel to each other if the angle condition as described above is satisfied. In one example, in order to further improve the efficiency of fine particle separation and/or alignment, the inclined grooves may be parallel to each other or at an angle of 0° to 30°, 0° to 25°, 0° to 20°, 0° to 15°, 0° to 10°, 0° to 5°, or 0° to 3°, but not limited thereto.

In addition, if the one or more inclined grooves(s) as formed satisfy the angle condition and can be structurally separated from the neighboring inclined grooves (especially from the inclined grooves positioned in the neighborhood in a direction from the one end to the other end), the inclined grooves do not need to be positioned in a straight line in the inclined direction. Accordingly, while the inclined grooves may be positioned in a straight line in the inclined direction for more efficient fine particle separation and/or alignment, the embodiments are not limited thereto.

FIG. 9 illustrates an exemplary arrangement of one or more inclined grooves as formed (the inclined grooves are shown in dark color; a white arrow indicates the direction (the main moving direction of the fluid) from one end where the inlet part is positioned to the other end; and a black arrow indicates the fine particle moving direction). In one example, the center of one or more inclined grooves may be arranged to be positioned in a straight line in a direction perpendicular to the inclined side, as illustrated in FIG. 9A. In another example, as illustrated in FIG. 9B, the one or more inclined grooves positioned in the neighboring rows in a direction (indicated by the white arrow) from the one end where the inlet part is positioned to the other end may be arranged in a position that is shifted to the fine particle moving direction (to a direction of the side surface where the fine particle discharge part is positioned; indicated by the black arrow) with respect to the center position of the grooves. In yet another example, as illustrated in FIG. 9C, the one or more inclined grooves positioned in the neighboring rows in a direction (indicated by the white arrow) from the one end where the inlet part is positioned to the other end may be arranged in a position that is shifted in an opposite direction from the fine particle moving direction (opposite from a direction where the fine particle discharge part is positioned; indicated by the black arrow) with respect to the center position of the grooves. Among these various arrangements, the separation efficiency of the fine particles is the most excellent with an arrangement similar to that of FIG. 9A. As shown in FIG. 9B, even in the case of having an arrangement shifted toward the fine particle moving direction, excellent fine particle separation efficiency can also be obtained. In this case, for a higher fine particle separation efficiency, the distance that the inclined grooves are shifted in the fine particle moving direction may be within the length (lr in FIG. 4B) (may include 0) in the inclined direction of the inclined groove, such as, for example, within ⅘, within ⅗, within ¾, within ⅔, or within ½ (may include 0) of the length of the inclined direction of the inclined grooves. In the case of the arrangement of FIG. 9C, the fine particle separation efficiency may be somewhat lowered compared with the arrangements FIGS. 9A and 9B.

As described above, since the inclined grooves have different space height (depth) from the channel part, the flow direction and rate of the fluid are different from the channel part, and accordingly, the fine particles included in the fluid are subjected to a force of different type and components (direction and size) than those of the channel part, and as a result, the fine particle are collected in one direction as a movement pattern thereof is changed.

In order to induce the specific fine particle movement in the inclined grooves to separate the fine particles from the fluid, the inclined groove should be a space that does not easily allow the fine particles to enter against the movement of the fluid generated when the fine particles to be separated from the inlet part pass through the channel part. Accordingly, the height or depth of the inclined grooves (denoted by $h_r$ in FIG. 4A), the width in a direction perpendicular to the inclined side (denoted by $w_r$ in FIG. 4A), and the length in the inclined direction (denoted by $l_r$ in FIG. 4B) may be appropriately adjusted in accordance with the size of the fine particles to be separated.

When two or more fine particles having different average particle diameters are present in the fluid, the fine particles having the largest average particle size may be separated and/or aligned by the technologies described herein. For example, when the fluid is blood and the fine particles to be separated are leukocytes, and when the inclined groove is a space where the blood cells (erythrocytes, platelets, etc.) smaller than leukocytes can easily pass against the flow of blood generated when the blood from the inlet part is passed through the channel part, but the leukocytes cannot pass, the leukocytes are separated from the other blood components and moved in a direction perpendicular to the inclined direction where the inclined groove is formed.

The height (depth: $h_r$) of the one or more inclined grooves may be equal to or different from each other.

In one example, the height (or depth) of the inclined groove may be 0.5 to 10 times, 0.5 to 7 times, 0.5 to 5 times, 0.5 to 4 times, 0.5 to 3 times, 0.5 to 2 times, 0.5 to 1.5 times, 0.5 to 1 time, 0.7 to 10 times, 0.7 to 7 times, 0.7 to 5 times, 0.7 to 4 times, 0.7 to 3 times, 0.7 to 2 times, 0.7 to 1.5 times, 0.7 to 1 time, 1 to 10 times, 1 to 7 times, 1 to 5 times, 1 to 4 times, 1 to 3 times, 1 to 2 times, 1 to 1.5 times, 1.5 to 10 times, 1.5 to 7 times, 1.5 to 5 times, 1.5 to 4 times, 1.5 to 3 times, 1.5 to 2 times the average diameter of the fine particles to be separated and/or aligned.

In one example, when the fluid is blood and the fine particles to be separated and/or aligned are leukocytes, considering that the average diameter of the erythrocytes is about 8 um to 10 um, the thickness is about 2 um to 3 um, and the average diameter of leukocytes is about 15 um, the depth ($h_g$) of the inclined groove may be 7 to 150 μm, 7 to 105 μm, 7 to 75 μm, 7 to 60 μm, 7 to 45 μm, 7 to 30 μm, 7 to 23 μm, 7 to 15 um, 10 to 150 um, 10 to 105 um, 10 to 75 um, 10 to 60 um, 10 to 45 um, 10 to 30 um, 10 to 23 um, 10 to 15 um, 15 to 150 um, 15 to 105 um, 15 to 75 um, 15 to 60 um, 15 to 45 um, 15 to 30 um, 15 to 23 um, 22 to 150 um, 22 to 105 um, 22 to 75 um, 22 to 60 um, 22 to 45 um, or 22 to 30 um.

The width ($w_r$) in a direction perpendicular to the inclined side of the inclined groove may be equal to or different from the depth ($h_r$) of the groove. Further, the widths of one or more inclined grooves as formed may be the equal to or different from each other. For example, the width in the perpendicular direction of the inclined side of the inclined groove may be 0.5 to 10 times, 0.5 to 7 times, 0.5 to 5 times, 0.5 to 4 times, 0.5 to 3 times, 0.5 to 2 times, 0.5 to 1.5 times, 0.5 to 1 time, 0.7 to 10 times, 0.7 to 7 times, 0.7 to 5 times, 0.7 to 4 times, 0.7 to 3 times, 0.7 to 2 times, 0.7 to 1.5 times, 0.7 to 1 time, 1 to 10 times, 1 to 7 times, 1 to 5 times, 1 to 4 times, 1 to 3 times, 1 to 2 times, 1 to 1.5 times, 1.5 to 10 times, 1.5 to 7 times, 1.5 to 5 times, 1.5 to 4 times, 1.5 to 3 times, or 1.5 to 2 times the average diameter of the fine particles to be separated and/or aligned.

The height of the channel part (denoted by $h_c$ in FIG. 4A) may be 0.5 to 10 times, 0.5 to 7 times, 0.5 to 5 times, 0.5 to 4 times, 0.5 to 3 times, 0.5 to 2 times, 0.5 to 1.5 times, 0.5 to 1 time, 0.7 to 10 times, 0.7 to 7 times, 0.7 to 5 times, 0.7 to 4 times, 0.7 to 3 times, 0.7 to 2 times, 0.7 to 1.5 times, 0.7 to 1 time, 1 to 10 times, 1 to 7 times, 1 to 5 times, 1 to 4 times, 1 to 3 times, 1 to 2 times, 1 to 1.5 times, 1.5 to 10 times, 1.5 to 7 times, 1.5 to 5 times, 1.5 to 4 times, 1.5 to 3 times, or 1.5 to 2 times the average diameter of the fine particles, but not limited thereto.

For example, when the fluid is blood, any height of the channel part may be sufficient if it allows the blood cell components, for example, erythrocytes to pass therethrough, and is not particularly limited (since leukocytes are larger than erythrocytes but are amorphous, leukocytes can be transformed in accordance with the channel height by the flow rate of the blood and pass through the channel). For example, when the fluid is blood, the height of the channel part may be 2 to 20 um, 2 to 17 um, 2 to 15 um, 2 to 12 um, 5 to 20 um, 5 to 17 um, 5 to 15 um, 5 to 12 um, 7 to 20 um, 7 to 17 um, 7 to 15 um, 7 to 12 um, 10 to 20 um, 10 to 17 um, 10 to 15 um, or 10 to 12 um, but not limited thereto.

There is no particular restriction on the interval between one or more inclined grooves as formed in a direction (the main moving direction of fluid) from the one end where the inlet part of the passage part is positioned toward the other end. For example, it can be appropriately selected in the width range in a direction perpendicular to the inclined side of the inclined groove described above. In addition, if three or more inclined grooves are formed in the main moving direction of the fluid at two or more intervals therebetween, the respective intervals may be same as or different from each other.

Further, the length (denoted by $l_r$ in FIG. 4B) of the inclined groove in the inclined direction is not particularly limited, but may be adjusted in accordance with a size of the passage part (i.e., size of the chip) and/or the number of inclined directions of one inclined groove.

In another aspect, the number of one or more inclined grooves formed in the inclined direction may be adjusted in accordance with the size of the passage part (i.e., size of the chip) and/or the length of the inclined groove in the inclined direction.

The lengths ($l_r$) of one or more inclined grooves in the inclined direction may be equal to or different from each other.

In one example, the length of the inclined groove in the inclined direction may be at least 1 time, at least 1.5 times, at least 2 times, at least 2.5 times, at least 3 times, at least 3.5 times, at least 4 times, or at least 4.5 times the average diameter of the fine particles to be separated, such as, 1 to 20 times, 1.5 to 20 times, 2 to 20 times, 2.5 to 20 times, 3 to 20 times, 3.5 to 20 times, 4 to 20 times, 4.5 to 20 times, 1 to 15 times, 1.5 to 15 times, 2 to 15 times, 2.5 to 15 times, 3 to 15 times, 3.5 to 15 times, 4 to 15 times, 4.5 to 15 times, 1 to 10 times, 1.5 to 10 times, 2 to 10 times, 2.5 to 10 times, 3 to 10 times, 3.5 to 10 times, 4 to 10 times, 1 to 7 times, 1.5 to 7 times, 2 to 7 times, 2.5 to 7 times, 3 to 7 times, 3.5 to 7 times, 4 to 7 times, 4.5 to 7 times, 1 to 5 times, 1.5 to 5 times, 2 to 5 times, 2.5 to 5 times, 3 to 5 times, 3.5 to 5 times, 4 to 5 times, or 4.5 to 5 times the average diameter of the erythrocytes, but not limited thereto.

Any interval (denoted by $l_r$ in FIG. 4B) in the inclined direction between the inclined grooves may be sufficient if it is not less than the minimum interval that can physically divide two or more inclined grooves, and the upper limit is not particularly limited, although it may be shorter than the length of the inclined groove in consideration of the separation efficiency of the fine particles. In one example, the interval between the inclined grooves may be 0.001 times or more, 0.01 times or more, or 0.1 times or more the average diameter of the fine particles to be separated, such as, for example, 0.001 to 10 times, 0.001 to 5 times, 0.001 to 3 times, 0.001 to 2 times, 0.001 to 1 time, 0.01 to 10 times, 0.01 to 5 times, 0.01 to 3 times, 0.01 to 2 times, 0.01 to 1 time, 0.1 to 10 times, 0.1 to 5 times, 0.1 to 3 times, 0.1 to 2 times, or 0.1 to 1 time the average diameter of the fine particles to be separated, but not limited thereto.

The inlet part is a portion to which the fluid is introduced and/or the introduced fluid is supplied to the passage part.

The inlet part may be connected directly to the passage part or optionally, may be connected to the passage part through a cavity that includes an empty space in fluid communication with the inlet part and the passage part. The inlet part may be positioned on one end of the passage part, and by the 'one end', it means the upstream area of the passage part where the flow of fluid starts.

The fine particle discharge part is a portion where fine particles are separated and/or aligned. The one side surface on which the discharge part is positioned may mean: a side surface of the passage part at an angle (the angle of the line perpendicular to both side surfaces with respect to the inclined groove (i.e., the center line in the longitudinal direction of the inclined groove) of greater than 0° and less than 90° with the inclined groove; a portion of the end connected to the side surface (i.e., a portion of the other end with respect to the one end where the inlet part is positioned; simply, 'other end'); or a corner at which the side surface and the other end are connected.

The fluid discharge part through which the fluid from which the fine particles are separated (removed) is discharged may mean: an opposite side surface ('other side surface') to the one side surface where the fine particle discharge part is positioned; a portion of an end connected to the other side surface (i.e., a portion of the other end with respect to the one end where the inlet part is positioned; simply, 'other end'); or a corner at which the other side surface and the other end are connected.

The fine particle discharge part and the fluid discharge part may be connected directly to the passage part or optionally, may be connected to the passage part through a cavity that includes an empty space in communication with the discharge part and the passage part.

The 'side surface' means both side surfaces of the passage part with respect to the main moving direction of the fluid (i.e., a direction from one end where the inlet part is positioned to the other end). In one example, the chip for separating and/or aligning the fine particles may be a structure including a substrate (i.e., surface on which irregularities are not formed; denoted by '200' in FIGS. 4A and 4B), a surface on which irregularities are formed (i.e., surface on which one or more inclined grooves are formed to be inclined), and both side surfaces.

The one end where the inlet part is positioned and the other end may be both open or partially open.

In an example, the substrate, both side surfaces, and the surface formed with irregularities may be made of the same solid material, or different solid materials from each other, in which the specific materials are not particularly limited.

The substrate, both side surfaces, and the surface having the irregularities formed may be made of a material independently selected from the group consisting of: a commonly used polymer such as polystyrene (PS), polycarbonate (PC), polymethylmethacrylate (PMMA), polyethylene terephthalate (PET), polydimethylsiloxane (PDMS), or the like; a photoresist material such as SU-8, polyethylene glycol diacrylate (PEG-DA), or the like; a metal such as aluminum, iron, platinum, and copper; a soft solid such as silicon; and glass, or the like, but not limited thereto.

The size of the chip for separating and/or aligning the fine particles is not particularly limited, but by way of example, the length (in the direction from one end to the other end; which is the main moving direction of the fluid) may be about 1 mm to about 100 mm, about 1 mm to about 50 mm, about 1 mm to about 30 mm, about 1 mm to about 20 mm, or about 1 mm to about 10 mm, and the width may be about 100 um to about 2000 um, about 100 um to about 1800 um, about 100 um to about 1500 um, about 100 um to about 1300 um, about 100 um to about 1000 um, about 300 um to about 2000 um, about 300 um to about 1800 um, about 300 um to about 1500 um, about 300 um to about 1300 um, or about 300 um to about 1000 um, but not limited thereto.

Another example provides a device for separating and/or aligning fine particles including one or more chips for separating and/or aligning fine particles, in which the device may include, for example, two or more, four or more, six or more, or eight or more chips for separating and/or aligning fine particles.

The upper limit of the number of chips included in the device for separating and/or aligning fine particles is not limited, and accordingly, may include any number of chips as long as it is allowed by the spatial conditions of the device for separating and/or aligning fine particles.

For example, the number of chips included in the device for separating and/or aligning fine particles may be 1 to 100, 1 to 80, 1 to 60, 1 to 50, 1 to 40, 1 to 30, 1 to 20, 1 to 10, 2 to 100, 2 to 80, 2 to 60, 2 to 50, 2 to 40, 2 to 30, 2 to 20, 2 to 10, 4 to 100, 4 to 80, 4 to 60, 4 to 50, 4 to 40, 4 to 30, 4 to 20, 4 to 10, 6 to 100, 6 to 80, 6 to 60, 6 to 50, 6 to 40, 6 to 30, 6 to 20, 6 to 10, 8 to 100, 8 to 80, 8 to 60, 8 to 50, 8 to 40, 8 to 30, 8 to 20, or 8 to 10, but not limited thereto.

The amount of fluid that can be processed in a device for separating and/or aligning one fine particles may be increased in multiples in proportion to the number of chips for separating and/or aligning fine particles included in a device for separating and/or aligning fine particles. The two or more chips for separating and/or aligning the fine particles included in the device for separating and/or aligning the fine particles may be connected in parallel.

The device for separating and/or aligning fine particles may be may further include one or more cavity-type inlet parts connected to the inlet part of each chip (designed to supply fluid to the inlet part of each chip), and/or one or more cavity-type fine particle discharge parts connected to the discharge part of each chip (designed to collect fine particles separated from each fine particle discharge part).

In another example, when one or more of the two or more chips for separating and/or aligning fine particles included in the device for separating and/or aligning fine particles further include the fluid discharge part to separate the fluid from which the fine particles have been removed: on an opposite surface to the fine particle discharge part, that is, on an opposite side surface to the one side surface on which the fine particle discharge part is positioned; on the other end connected to the one side surface; or on a corner at which the side surface and the other end are connected at the corner, the device for separating and/or aligning fine particles may further include a cavity-type fluid discharge part (designed to collect the fluid from which fine particles have been removed, each being collected at each fluid discharge part) connected to the one or more fluid discharge parts.

In one example, when the fine particles to be separated are leukocytes and the fluid is blood, leukocytes may be collected in the fine particle discharge part of the device for separating and/or aligning fine particles or the cavity-type fine particle discharge part, and leukocyte-free blood may be collected in the cavity-type fluid discharge part.

The device for separating and/or aligning the fine particles may further include a fine particle reservoir and/or a fluid reservoir for collecting and/or storing the fine particles discharged from two or more chips for separating and/or aligning the fine particles and the fine particles and/or the fluid from which the fine particles have been removed.

The chip and/or device for separating and/or aligning the fine particles may use the flow of fluid which may be generated by the flow rate of the injected fluid in a direction from the one end where the injection part is positioned to the opposite end.

Any injection rate of fluid would be sufficient if it is not less than the minimum flow rate necessary to cause the flow of the fluid.

For example, the injection rate of fluid for each of the chips for separating and/or aligning the fine particles may be about 10 ul/min or more, about 20 ul/min or more, about 30 ul/min or more, about 40 ul/min or more, about 50 ul/min or more, about 60 ul/min or more, 70 ul/min or more, or about 80 ul/min or more, and the upper limit may be an order of about 1000 ul/min, about 900 ul/min, about 800 ul/min, about 700 ul/min, about 600 ul/min, about 500 ul/min, about 450 ul/min, about 400 ul/min, about 350 ul/min, about 300 ul/min, about 250 ul/min, about 200 ul/min, about 150 ul/min, or about 120 ul/min, but not limited thereto.

The fluid injection rate of the device for separating and/or aligning the fine particles may be set to be increased in multiples of the fluid injection rates of the chips for separating and/or aligning the fine particles included in the device, according to the number of chips for separating and/or aligning the fine particles.

In one example, the chip for separating and/or aligning the fine particles described above and/or a device for separating and/or aligning fine particles described above may be used in connection with a supply part that can supply fluid to the fluid inlet part.

In another example, there is provided a kit for separating and/or aligning fine particles including:

the chip for separating and/or aligning the fine particles described above or the device for separating and/or aligning the fine particles described above, and a fluid supply part connected to the fluid inlet part of the chip for separating and/or aligning the fine particles, or to the fluid inlet part of the device for separating and/or aligning the fine particles.

The fluid supply part may serve to apply a fluid injection rate by means of storing and/or compressing the fluid, and for example, may be one or more selected from the group consisting of a syringe, a pipette, a pump such as a piston pump, a syringe pump, a diaphragm pump, a peristaltic pump, or the like.

In one example, the fluid inlet part of the device for separating and/or aligning the fine particles may be used in the form of a fluid inlet part connected with a syringe needle.

Another example provides a method for separating and/or aligning fine particles using the chip for separating and/or aligning fine particles as described above and/or the device for separating and/or aligning fine particles described above.

Specifically, the method for separating and/or aligning the fine particles may include:

supplying a fluid including fine particles to the inlet part of the chip for separating and/or aligning fine particles described above and/or to the inlet part of the device for separating and/or aligning fine particles described above; and collecting fine particles discharged from the fine particle discharge part of the chip for separating and/or aligning the fine particles described above or from the fine particle discharge part of the device for separating and/or aligning the fine particles described above.

When the chip for separating and/or aligning fine particles and/or the device for separating and/or aligning fine particles further includes a fluid discharge part for discharging the fluid from which the fine particles have been removed, the method for separating and/or aligning the fine particles may further include after the step of supplying the fluid, and before or after, or simultaneously with the step of collecting the fine particles, collecting the fluid from which the fine particles have been removed, which is discharged from the fluid discharge part of the chip for separating and/or aligning fine particles and/or the fluid discharge part of the device for separating and/or aligning fine particles.

In one specific exemplary embodiment, when the fine particles are leukocytes and the fluid is blood, there is provided a method for separating and/or removing leukocytes from blood is provided, including:

supplying the blood to the inlet part of the chip for separating and/or aligning fine particles described above and/or to the inlet part of the device for separating and/or aligning fine particles described above; and collecting leukocytes discharged from the fine particle discharge part of the chip for separating and/or aligning the fine particles described above or from the fine particle discharge part of the device for separating and/or aligning the fine particles described above.

In a specific exemplary embodiment, when the chip for separating and/or aligning fine particles and/or the device for separating and/or aligning fine particles further includes a fluid discharge part for the fluid from which the fine particles have been removed, and when the fine particles are leukocytes and the fluid is blood, there is provided a method for separating and/or removing leukocytes from blood or a method for obtaining leukocyte-free blood is provided, including:

supplying the blood to the inlet part of the chip for separating and/or aligning fine particles described above and/or to the inlet part of the device for separating and/or aligning fine particles described above;

collecting leukocytes discharged from the fine particle discharge part of the chip for separating and/or aligning the fine particles described above or from the fine particle discharge part of the device for separating and/or aligning the fine particles described above; and collecting the blood from which the leukocytes have been removed, which is discharged from the fluid discharge part of the chip for separating and/or aligning the fine particles described above or from the fluid discharge part of the device for separating and/or aligning the fine particles described above.

The method for separating and/or removing leukocytes from the blood or the method for obtaining leukocyte-free blood has an advantage in that leukocytes can also be efficiently separated even from whole blood or blood having a relatively high concentration of blood cells. In one example, the injected blood may be the whole blood, or whole blood (1 to 1/20 concentration) diluted 1 to 20 times by volume with respect to whole blood, but not limited thereto.

According to the method for separating and/or aligning the fine particles, the recovery rate of the fine particles from the fluid may be about 10% or more, about 30% or more, about 50% or more, about 60% or more, about 70% or more, about 80% or more, about 90% or more, about 92% or more, about 95% or more, about 96% or more, about 97% or more, about 98% or more, about 99% or more, 99.5% or more, or 99.9% or more, on the basis of the total number of particles contained in the fluid before supplying the chip or device. In addition, the fine particles loss rate ([(Total number of particles contained in the fluid before supply to the chip or device—total number of separated fine particles)/total number of particles contained in the fluid before supply to the chip or device]*100) may be about 90% or less, about 70% or less, about 50% or less, about 40% or less, about 30% or less, about 20% or less, about 10% or less, about 8% or less, about 5% or less, about 4% or less, about 3% or less, about 2% or less, about 1% or less, about 0.5% or less, or about 01% or less.

When the microparticles are leukocytes and the fluid is blood, according to the method for separating and/or removing the leukocytes, or according to the method for obtaining leukocyte-free blood, the recovery rate of leukocytes from blood may be about 10% or more, about 30% or more, about 50% or more, about 60% or more, about 70% or more, about 80% or more, about 90% or more, about 92% or more, about 95% or more, about 96% or more, about 97% or more, about 98% or more, about 99% or more, 99.5% or more, or 99.9% or more, on the basis of the total number of leukocytes initially contained in the blood. The loss rate of the leukocytes may be about 90% or less, about 70% or less, about 50% or less, about 40% or less, about 30% or less, about 20% or less, about 10% or less, about 8% or less, about 5% or less, about 4% or less, about 3% or less, about 2%, about 1% or less, about 0.5% or less, or about 0.1% or less.

The leukocyte separating efficiency may be related to the amount of blood injection (for example, higher the leukocytes separating efficiency may be obtained when a smaller the amount of blood is injected), and in order to further increase the leukocytes separation efficiency, the amount of blood injection (injection rate) applied to one chip may be adjusted within a range of: from about 10 to about 1000 ul/min, from about 10 to about 900 ul/min, from about 10 to about 800 ul/min, from about 10 to about 700 ul/min, from about 10 to about 600 ul/min, from about 10 to about 500 ul/min, from about 10 to about 400 ul/min, from about 10 to about 350 ul/min, from about 10 to about 300 ul/min, from about 10 to about 250 ul/min, from about 10 to about 200 ul/min, from about 10 to about 150 ul/min, from about 50 to about 1000 ul/min, from about 50 to about 900 ul/min, from about 50 to about 800 ul/min, from about 50 to about 700 ul/min, from about 50 to about 600 ul/min, from about 50 to about 500 ul/min, from about 50 to about 400 ul/min, from about 50 to about 350 ul/min, from about 50 to about 300 ul/min, from about 50 to about 250 ul/min, from about 50 to about 200 ul/min, or from about 50 to about 150 ul/min.

The method for separating and/or removing leukocytes from the blood, or the method for obtaining leukocyte-free blood, and/or the chip for separating and/or aligning fine particles used the method and/or the device for separating and/or aligning fine particles used for the method may be usefully applied to an example in which it is necessary to: remove leukocytes from donated blood for blood transfusion; or separate leukocytes from patient's blood to obtain leukocytes from the patient's blood for use in testing or diagnosis.

Advantageous Effects

The device for separating and/or aligning the fine particles according to an exemplary embodiment of the present disclosure aims to separating and aligning the fine particles in a desired direction based on a control of pattern shape.

In addition, the device for separating and aligning the fine particles according to an exemplary embodiment of the present disclosure aims to separating and aligning the fine particles in a desired direction more economically and conveniently by means of a pattern shape.

It is to be understood that the technical objectives to be achieved by the present disclosure are not limited to those mentioned above and other technical problems that are not mentioned will be apparent to those skilled in the art from the following description.

Figure 1:
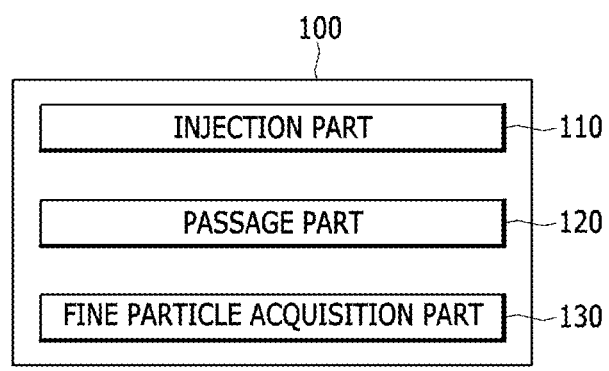
FIG. 1 schematically illustrates a configuration of a device for separating and aligning the fine particles according to an exemplary embodiment of the present disclosure.

(Description of Reference Numerals in the Drawings)

| | |
|---|---|
| 100: device for separating and aligning the fine particles | |
| 110: injection part | 120: passage part |
| 130: fine particle acquisition (or collection) part | |
| 210: leukocytes | 220: erythrocytes |

MODE FOR INVENTION

The above and other objects, features and advantages of the present disclosure will become more apparent from the following detailed description of the present disclosure when taken in conjunction with the accompanying drawings. First, the terms used in the present application are used only to describe a specific exemplary embodiment, and are not intended to limit the present disclosure, and unless otherwise specified, a singular expression includes a plural expression. In addition, the expression "comprise" or "have" as used herein is intended to designate an existence of steps, operations, elements, components or a combination of these, and accordingly, should not be understood as precluding an existence or a possibility of adding one or more of other characteristics, numbers, steps, operations, elements, components or a combination of these.

Hereinafter, the above and other objects, features and advantages of the present disclosure will become more apparent from the following detailed description of the present disclosure when taken in conjunction with the accompanying drawings.

FIG. 1 schematically illustrates a configuration of a device for separating and aligning the fine particles according to an exemplary embodiment of the present disclosure. As shown in FIG. 1, the device 100 for separating and aligning fine particles may include a blood injection part (inlet part) 110, a passage part 120, and a fine particle collection part (fine particle discharge part) 130.

Specifically, a fluid including fine particles desired to be acquired may be injected through the injection part 110, and the injected fluid flows through the passage part 120 and the fine particles are concentratedly separated in one direction and the fluid including the separated fine particles can be concentrated in the fine particle collection part 130.

The injection part 110, the passage part 120, and the fine particle collection part 130 will be described in more detail.

A fluid including fine particles may be injected into the injection part 110.

For example, the injection may be performed via a tube, syringe, pipette, or the like, and the fluid may include whole blood from which leukocyte acquisition(collection) is intended.

The passage part 120 may separate the fine particles in a specific direction during the flow of the injected fluid. More specifically, while the fluid injected through the injection part 110 flows in the passage part 120, the fine particles may be separated in a predetermined direction to be flowed. Accordingly, by providing the fine particle collection part 130 at the end of the predetermined direction, the fluid including the separated fine particles may be acquired.

The fine particle separation may be performed through a pattern of a certain shape in the passage part 120, which has a predetermined angle of inclination with respect to a perpendicular direction to the main flow direction of the fluid, in which the inclination of the pattern may be determined according to the main moving direction of the fluid and the specific direction in which the fine particles are to be separated. For example, the pattern of the passage part 120 may have an inclination that is inclined in the opposite direction to the specific direction in which the fine particles is to be separated, with respect to a perpendicular direction to the main flow direction of the fluid, and the inclination may include inclination of 45 degrees or less with respect to the main flow direction of the fluid. By this inclination, when a fluid including fine particles is flowed, the fine particles move in a direction perpendicular to the inclined pattern grooves, thus flowing mainly in a certain direction.

The pattern in the passage part 120 may include a groove shape, and the groove shape of the pattern, that is, at least one of the height, width, length of the groove and height of the passage part may be determined according to the kind of the fine particles to be separated.

More specifically, the height and width of the groove may be within 0.5 to 2 times the diameter of the fine particle, the height of the groove is within 3 to 5 times the average diameter of the leukocytes the diameter of the fine particle, and the height of the passage part is within 1.5 to 2 times the diameter of the fine particle. The diameter includes an average diameter of the fine particles.

In addition, the pattern in the passage part 120 may include the grooves formed to be arranged at a predetermined interval, and the predetermined interval may include about 50 um (micrometers).

In addition, the shape of the groove may be at least one of rectangle, rhombic, triangle, ellipse, and star, but not limited thereto.

Since the fine particles moving in a specific direction through the pattern stay in the perpendicular position in the passage part 120 even in the area without the pattern by the laminar flow of the fluid, it is possible to acquire the fluid having a high concentration of fine particles through the fine particle collection part 130 positioned at the end.

The construction of the pattern of the passage part 120 and the resulting flow of the fluid will be described in detail below with reference to FIGS. 3, 4A and 4B which specifically show the corresponding embodiment.

The fine particle collection part 130 may acquire the separated fine particles. More specifically, since the fine particles can be concentratedly separated and flow in a predetermined direction by the passage part 120, the fine particle collection part 130 may be installed at the end of the predetermined direction to acquire the separated fine particles.

For example, as shown in the drawings, leukocytes separation using whole blood can be performed through the device 100 for separating and aligning the fine particles having fine particle collection parts 130a and 130b.

That is, with the separating flow process through the passage part 120, the fine particle collection part 130a may acquire a high ratio of leukocytes, and accordingly, the fine particle collection part 130b may acquire a relatively high ratio of erythrocytes.

Meanwhile, the device for separating and aligning the fine particles may be made of polymer (e.g., polystyrene (PS), polycarbonate (PC), polymethylmethacrylate (PMMA), polydimethylsiloxane (PDMS), etc.) While the hydrophobic surface may separate and align the fine particles, it is preferable that the surface has hydrophilicity in consideration of the flow of the fluid.

Figure 2:
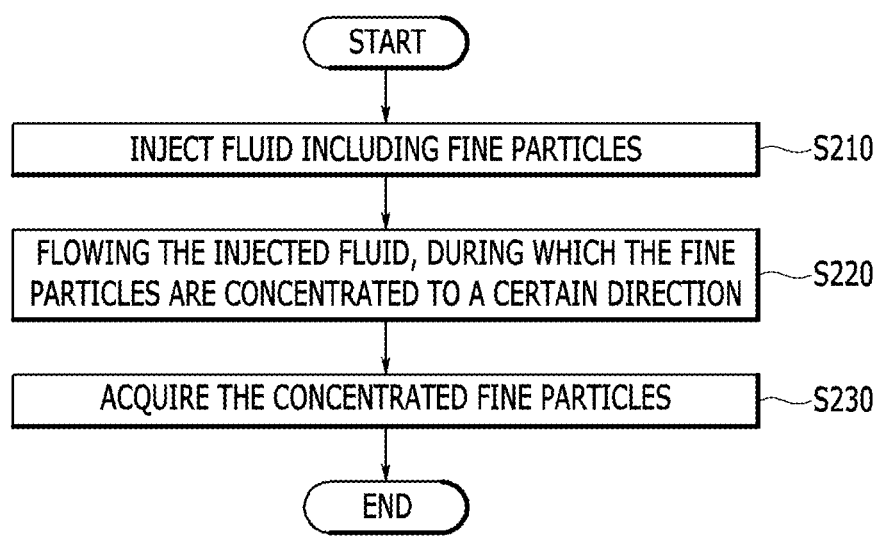
FIG. 2 is a flowchart showing a method for separating and aligning the fine particles according to an exemplary embodiment of the present disclosure.

FIG. 2 is a flowchart showing a method for separating and aligning the fine particles according to an exemplary embodiment of the present disclosure.

At S210, fluid including fine particles may be injected.

At S220, while the injected fluid flows, the fine particles may be concentratedly flowed in a predetermined direction. The flow concentrated in the predetermined direction may be a result of a passage part that has a pattern of a certain shape having a predetermined inclination angle with respect to a perpendicular direction to the main moving direction of the fluid. In addition, the pattern of a certain shape may include a groove shape formed at a predetermined interval.

At S230, fine particles concentrated in the predetermined direction may be acquired.

One example of the fine particles injection, separation, and acquisition (collection) process described above may be performed through the device 100 for separating or aligning the fine particles.

Figure 3:
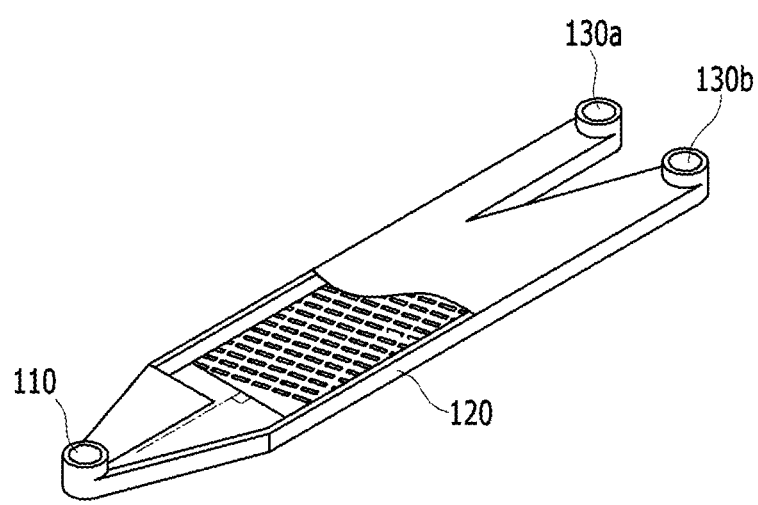
FIG. 3 is a view showing a device for separating and aligning the fine particles according to an exemplary embodiment of the present disclosure.
Figure 4A:
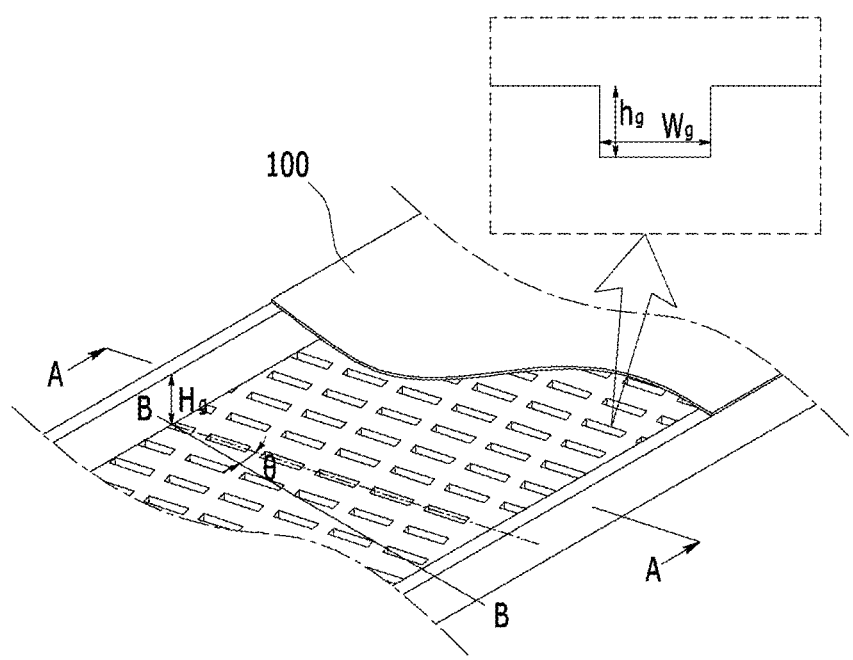
FIG. 4A is a view illustrating a passage part of a device for separating and aligning the fine particles according to an exemplary embodiment of the present disclosure.
Figure 4B:
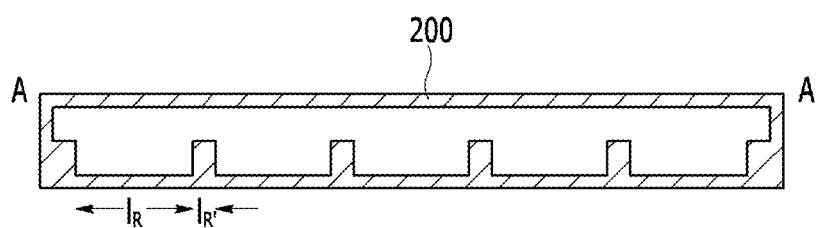
FIG. 4B is a cross sectional view taken on line A-A of FIG. 4A (200: substrate on which an inclined groove is not formed; A-A: inclined cross section; a-a: cross section perpendicular to the inclined cross section; B-B: line perpendicular to both side surfaces; θ: angle (inclined angle) between A-A and B-B; C: main moving direction of fluid (injection direction of fluid); D: fine particle moving direction (i.e., direction perpendicular to the inclined cross section (A-A) and the main moving direction of and fluid); hr: height of inclined groove (depth); wr: width in a direction perpendicular to the inclined side of the inclined groove; hc: height of the channel part; lr: length of the inclined groove in the inclined direction: lr': interval in inclined direction between the inclined grooves).

FIG. 3 is a view showing a device for separating and aligning the fine particles according to an exemplary embodiment of the present disclosure, and FIG. 4 is a detailed view showing a passage part of the device for separating and aligning the fine particles according to an exemplary embodiment of the present disclosure. As shown in the drawings, the device for separating and aligning the fine particles according to an exemplary embodiment of the present disclosure may include an injection part 110, a passage part 120, and a fine particle collection part 130.

When the fluid including fine particles is injected into the injection part 110, the device 100 for separating and aligning the fine particles allows the fluid to flow through the passage part 120 so that the fine particles flow separately in a predetermined direction, and the separated fine particles may be concentrated toward the fine particle collection part 130.

The separation described above may be performed through a pattern of a certain shape formed in the passage part 120, and the pattern of a certain shape may be determined according to the size and direction of the fine particles to be separated. Also, as shown in FIG. 3, the pattern may be inclined at a predetermined angle (θ) with respect to a perpendicular direction to the main flow direction of the fluid, and the predetermined angle may be within 45 degrees or less.

FIG. 3 illustrates separating leukocytes from the other whole blood components, in which, as shown in the drawings, the pattern is inclined by the predetermined angle (θ) on the basis of the dashed line (line perpendicular to the main flow direction of the fluid), so that the leukocytes can be concentratedly separated as the whole blood flows, and aligned in the direction of the fine particle collection part 130.

The passage part 120 will be described below in greater detail. As shown in FIG. 4, the pattern of a certain shape formed in the passage part 120 may be inclined at a predetermined angle (θ) with respect to the main flow direction of fluid, and the certain shape may include a groove shape.

At least one of the height ($H_g$) of the groove, the width ($W_g$) of the groove, the length ($L_g$) of the groove, and the height ($H_e$) of the passage part may be adjusted according to the size of the fine particles to be separated, and based on the diameter of the fine particles to be separated, the height ($H_g$) and the width ($W_g$) of the groove may be within 0.5 to 2 times the diameter of the fine particle, the length ($L_g$) of the groove may be within 3 to 5 times the diameter of the fine particle, and the height ($H_e$) of the passage part may be within 1.5 to 2 times the diameter of the fine particle. The diameter includes an average diameter of the fine particles.

Hereinafter, the present disclosure will be described in more detail with reference to Examples. It is to be understood by those skilled in the art that these embodiments are only for describing the present disclosure in more detail and that the scope of the present disclosure is not limited by these embodiments.

EXAMPLE 1: EXAMPLE OF LEUKOCYTE ACQUISITION (COLLECTION) FROM WHOLE BLOOD

Figure 5A:
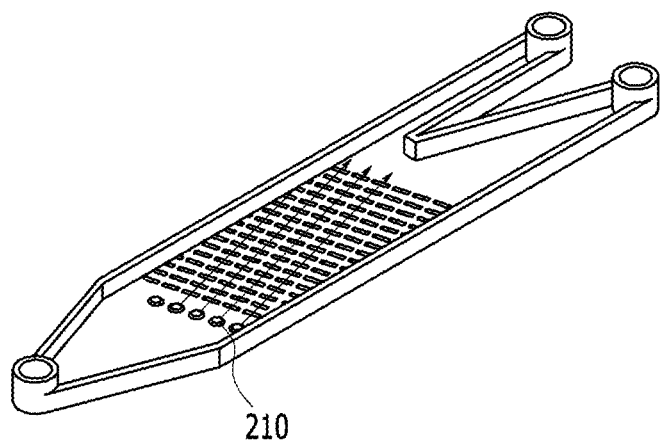
FIG. 5A is a view showing an example of using a device for separating and aligning the fine particles according to an exemplary embodiment of the present disclosure.
Figure 5B:
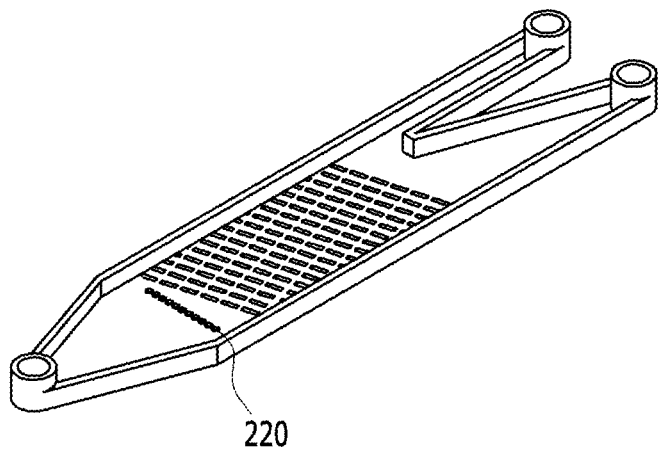
FIG. 5B is a view showing an example of using a device for separating and aligning the fine particles according to an exemplary embodiment of the present disclosure.
Figure 5C:
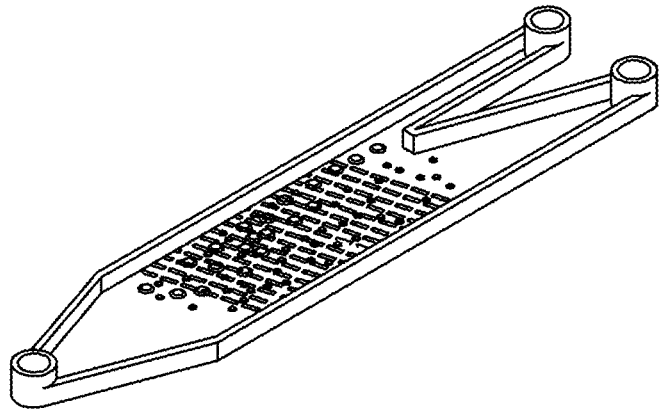
FIG. 5C is a view showing an example of using a device for separating and aligning the fine particles according to an exemplary embodiment of the present disclosure.

FIGS. 5A to 5C are views showing an example of using a device for separating and aligning the fine particles according to an exemplary embodiment of the present disclosure, in which, specifically, the white fine particles represent leukocytes, and the red fine particles represent erythrocytes, showing an exemplary embodiment of acquiring leukocytes from whole blood using the device for separating and aligning the fine particles.

Generally, leukocytes have an average diameter of 12 μm (micrometer) to 15 μm, and erythrocytes have an average diameter of 7 μm to 8 μm. According to this size difference, intensive acquisition of the leukocytes or erythrocytes can be realized through a pattern configuration in the passage part 120 of the device 100 for separating and aligning the fine particles.

That is, as shown in FIG. 5A, within the pattern of certain shape of the passage part 120, leukocytes of the whole blood can be concentratedly flow in the arrowed direction, and unlike the leukocytes, erythrocytes of the whole blood can flow without having a specific directionality, as shown in FIG. 5B. As a result, as shown in FIG. 5C, the leukocytes may be concentrated toward the fine particle collection part 130a, and the erythrocytes may be concentrated toward the fine particle collection part 130b.

More specifically, the height of the passage part 120, and the height, width, breadth, shape, or the like of the pattern groove in the passage part 120 may be adjusted to a predetermined size or shape so that the leukocytes are concentratedly flowed in a certain direction. Preferably, when the height of the passage part 120 is within 3 times the average diameter of the leukocytes, the height and width of the groove are within 0.5 to 2 times the average diameter of the leukocytes, and the length of the groove is within 3 to 5 times, a higher leukocyte acquisition rate can be provided.

In addition, the pattern is shaped to have a predetermined interval, and it is preferable that an interval of 50 um is provided between the pattern grooves so that the leukocytes are concentratedly flowed in a certain direction.

On the other hand, it is advantageous that the passage part 120 has a length of at least 500 μm or more so that leukocytes can flow in a certain direction.

Figure 5D:
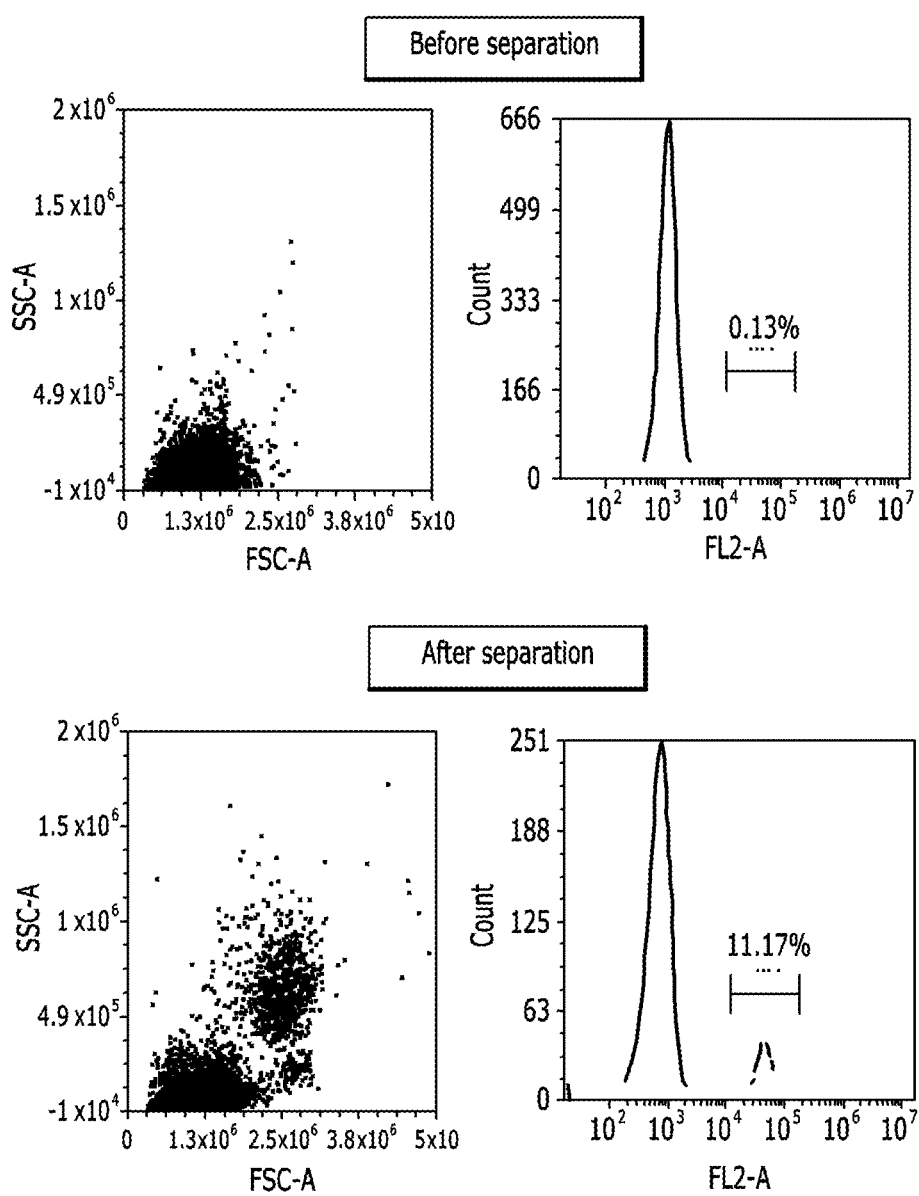
FIG. 5D is a graph showing a fine particle separation according to an example of using a device for separating and aligning the fine particles according to an exemplary embodiment of the present disclosure.

FIG. 5D is a graph showing a fine particle separation according to an example of using a device for separating and aligning the fine particles according to an exemplary embodiment of the present disclosure. The graph shows results of experiments that acquired leukocytes by injecting whole blood without dilution into an injection part, in which the height ($h_c$) of the passage part 120 (height of channel part) is 25 um, the height ($h_r$) of the groove is 25 um, the length ($l_r$) of the groove is 100 um, and the interval (Ir) of the pattern grooves is 20 um, and it can be seen that the concentrated leukocytes acquisition was possible by numbers about 100 times higher than that provided under the normal environment (0.13%→11.17%). Meanwhile, it is preferable that the height of the passage part 120 is 1.5 to 2 times the diameter of the fine particles to be separated.

That is, when the whole blood is injected into the device 100 for separating and aligning the fine particles according to an exemplary embodiment of the present disclosure, the device 100 is capable of separating the injected whole blood into high ratios of the leukocytes and the erythrocytes and aligning and acquiring them, thereby providing a much simpler and more economic structure as compared with the separation performed by way of the conventional centrifugal separator, dielectrophoretic separator, or the like.

EXAMPLE 2: EXAMPLE OF COMMON SEPARATION OF THE FINE PARTICLES OF A CERTAIN SIZE OR LARGER

Figure 6A:
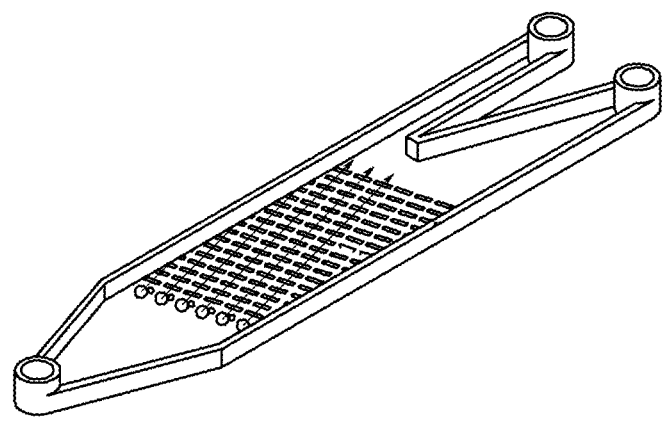
FIG. 6A is a view showing an example of using a device for separating and aligning the fine particles according to another exemplary embodiment of the present disclosure.
Figure 6B:
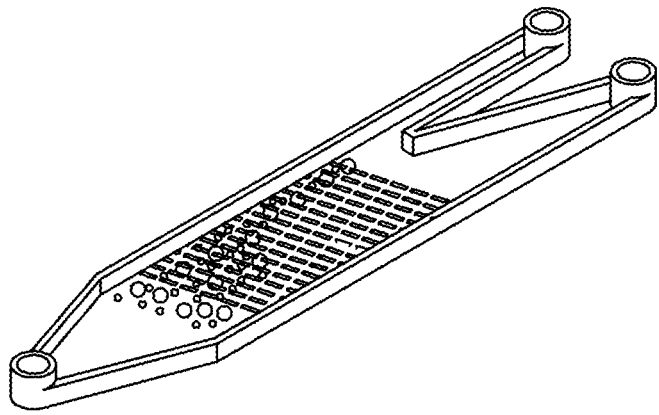
FIG. 6B is a view showing an example of using a device for separating and aligning the fine particles according to another exemplary embodiment of the present disclosure.

FIGS. 6A and 6B are views showing an example of using a device for separating and aligning the fine particles according to another exemplary embodiment of the present disclosure. As shown in the drawings, different kinds of fine particles can be concentratedly separated in one direction with the device for separating and aligning the fine particles according to another exemplary embodiment of the present disclosure.

More specifically, since it is enabled to select the fine particles to be separated according to sizes thereof and acquire them through a control of pattern shape of the passage part 120, it is possible to concentratedly separate the fine particles corresponding to a certain size category in one direction.

For example, by adjusting the total length of the passage part 120, the inclination, the shape, the height, the width, the length of the pattern groove, and the height of the passage part 120, according to the size of the fine particles to be separated, the fine particles to be separated and acquired can be concentratedly flowed in a certain direction.

EXAMPLE 3: YET ANOTHER EXEMPLARY EMBODIMENT FOR SEPARATING SPECIFIC FINE PARTICLES IN A CERTAIN DIRECTION

Figure 7A:
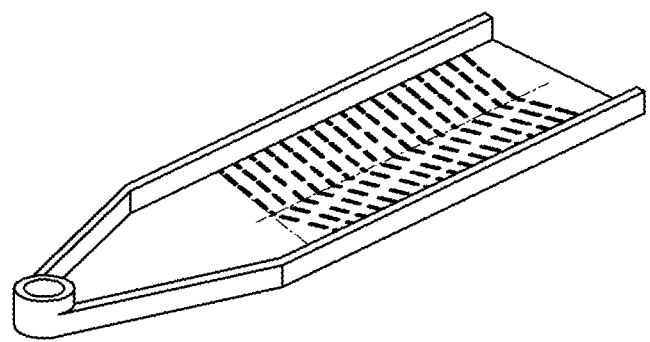
FIG. 7A is a view showing a device for separating and aligning the fine particles according to yet another exemplary embodiment of the present disclosure.
Figure 7B:
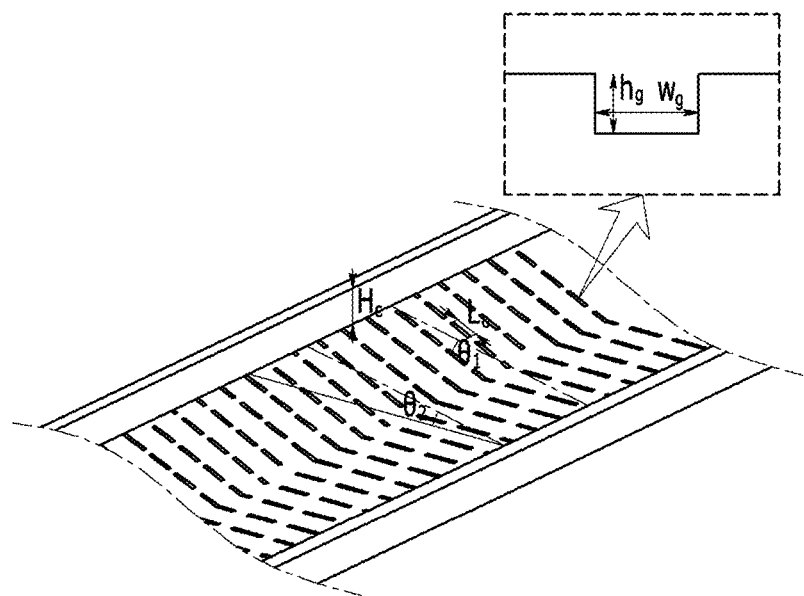
FIG. 7B is a detailed view showing a passage part of a device for separating and aligning the fine particles according to yet another exemplary embodiment of the present disclosure.
Figure 7C:
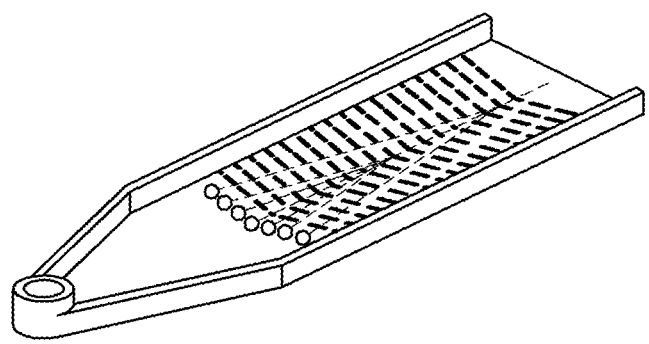
FIG. 7C is a view showing an example of using a device for separating and aligning the fine particles according to yet another exemplary embodiment of the present disclosure.
Figure 7D:
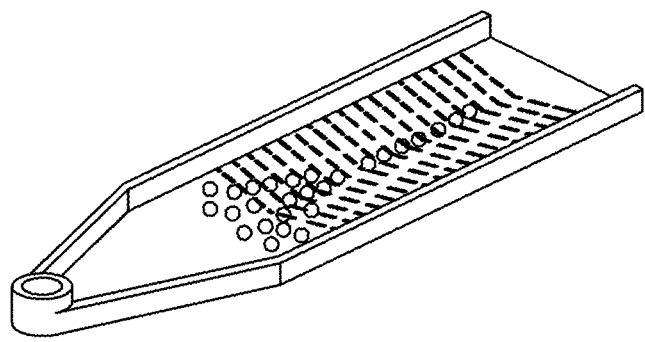
FIG. 7D is a view showing an example of using a device for separating and aligning the fine particles according to yet another exemplary embodiment of the present disclosure.

FIGS. 7A and 7B are views showing a device for separating and aligning the fine particles and a passage part thereof, according to another exemplary embodiment of the present disclosure, and FIGS. 7C and 7D are views showing an example of using a device for separating and aligning the fine particles according to yet another exemplary embodiment of the present disclosure.

As shown in FIGS. 7A to 7D, the device for separating and aligning the fine particles according to another exemplary embodiment of the present disclosure can concentrate fine particles in a predetermined direction, for example, toward the central portion of the passage part, or the like, by adjusting the shape of the pattern, or more particularly, the inclination of the pattern.

More specifically, as shown in FIGS. 7A and 7B, the pattern is formed to be inclined with respect to the main flow direction of the fluid, but the two patterns having different inclinations may be combined with each other such that the fine particles can be separated in one direction according to the inclinations between each other. The combination of the inclinations that is, the combination of the two patterns having different inclinations may result in angles formed in symmetry with each other based on a specific direction (for example, the central axis of the passage part).

In addition, the height of the pattern groove of the passage part 120 should be greater than the height of the entire passage part, and the height of the entire passage part should be within 1.5 to 2 times the minimum diameter of the fine particles to be transferred.

Meanwhile, regarding the separating effect obtained through the device for separating and aligning the fine particles, it is not quite necessary to consider the flow rate of the fluid, although it would be more preferable to maintain the flow rate of 150 um/s when the cross-sectional area of the passage part is 700 um*25 um. However, the separating effect can be maximized by adjusting appropriately the flow rate in accordance with the height and the width of the passage part, or the like.

Meanwhile, by adjusting the cross-sectional area of the passage part, or by combining a plurality of devices for separating and aligning the fine particles, a desired amount of fluid can be processed at a desired time to acquire specific fine particles. This will be described with reference to FIG. 8A.

PRACTICAL EXAMPLE

Figure 8A:
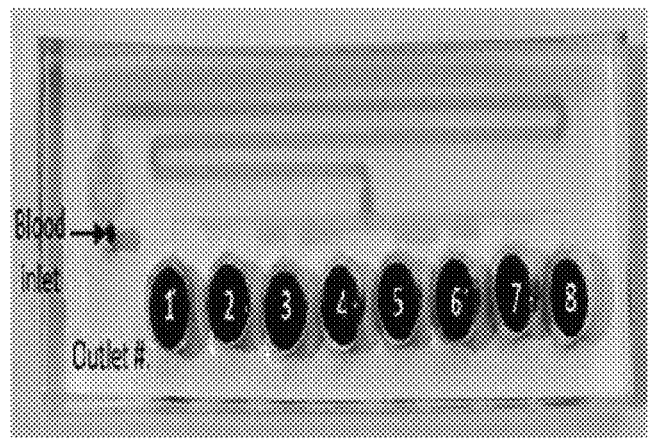
FIG. 8A is a view showing a Practical Example of using a device for separating and aligning the fine particles according to an exemplary embodiment of the present disclosure.
Figure 8B:
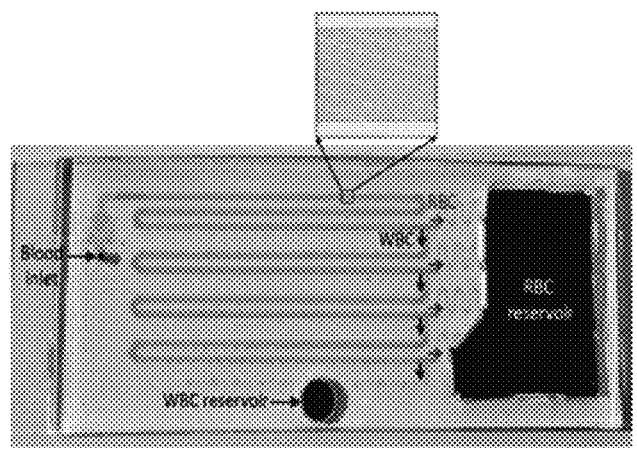
FIG. 8B is a view showing a Practical Example of using a device for separating and aligning the fine particles according to another exemplary embodiment of the present disclosure.
Figure 9:
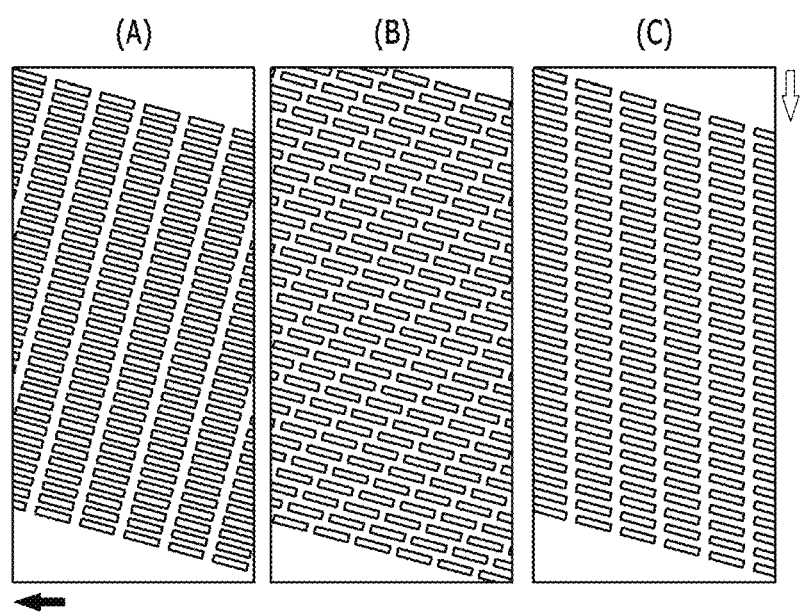
FIG. 9 illustrates an exemplary arrangement of one or more inclined grooves as formed (the inclined grooves are shown in dark color, in which a white arrow indicates the direction (the main moving direction of the fluid) from one end where the inlet part is positioned to the other end; and a black arrow indicates a moving direction of the fine particle being discharged).

Practical Example of a device for separating and aligning the fine particles according to an exemplary embodiment of the present disclosure FIG. 8A shows a Practical Example of using a device for separating and aligning the fine particles according to an exemplary embodiment of the present disclosure, and FIG. 8B is a view showing a Practical Example of using a device for separating and aligning the fine particles according to another exemplary embodiment of the present disclosure. Particularly, the drawings show a device for separating and aligning the fine particles, which is provided for concentratedly separating leukocytes from the whole blood, in which, when the whole blood is injected into the injection part (blood inlet) as illustrated, the injected whole blood passes through the passage part, during which the leukocytes flow in a certain direction, and the leukocytes can be concentratedly acquired from a specific fine particle collection part (Outlet #1, in the illustrated example) along the predetermined direction. As described above, the passage part may be a pattern of a certain shape having a predetermined degree of inclination, as shown in an enlarged view in FIG. 8B.

Meanwhile, as shown in FIGS. 8A and 8B, the device for separating and aligning the fine particles may include an injection part, a passage part, and a fine particle collection part, and the specific form of the constituent elements described above may be modified and applied in various ways within the scope of the technical idea of the present disclosure.

As described above, the device for separating and aligning the fine particles according to an exemplary embodiment of the present disclosure allows specific fine particles to be concentratedly flowed in a predetermined direction based on a pattern formed in a passage part, so that the fluid including a high concentration of the specific fine particles can be acquired. Accordingly, unlike conventional centrifuge, or the like, the fine particles can be acquired more economically and efficiently, and which can be advantageously applied in a variety of fields including plasma separation, blood cell separation from whole blood, water purification, flow cell for flow cytometry, or the like.

While the embodiments of the present disclosure have been described with reference to the accompanying drawings, those with ordinary knowledge in the technical field of the present disclosure will be able to understand that the present disclosure can be embodied into difference and more detailed modes, without departing from the technical concept or without modifying essential characteristics thereof. For example, the pattern of a certain shape formed in the passage part is not limited to those described above, and may be modified in various directions to achieve the object of the present disclosure, according to the type of microparticle desired to be obtained. Accordingly, the embodiments described above are to be considered in all respects as illustrative and not restrictive.

The invention claimed is:
1. A chip for separating or aligning fine particles comprising:

(i) a passage part in which a space where a fluid including fine particles which are capable of flowing is integrally formed and which has an inclined groove formed on one surface thereof;
(ii) an inlet part which is positioned on one end of the passage part and into which the fluid is introduced; and
(iii) a fine particle discharge part which is positioned on one side surface of the passage part,
wherein the groove includes one or more inclined grooves formed to be inclined at an angle greater than 0° and less than 90° with respect to a line which is perpendicular to both side surfaces of the passage part, and
wherein the fine particle discharge part is positioned at:
a side surface of the passage part with respect to a main moving direction of the fluid;
an end opposite to the one end of the passage part connected to the side surface of the passage part; or
a corner at which the side surface and the end opposite to the one end of the passage part are connected.

2. The chip of claim 1 for separating or aligning fine particles, wherein the inclined groove is formed to be inclined at an angle of greater than 0° and less than 45° with respect to a line perpendicular to both side surfaces of the passage part.

3. The chip of claim 1 for separating or aligning fine particles, wherein a depth of the inclined groove is 0.5 to 10 times an average diameter of the fine particles.

4. The chip of claim 1 for separating or aligning fine particles, wherein a width of an inclined side of the inclined groove in a direction perpendicular to both side surfaces of the passage part is 0.5 to 10 times an average diameter of the fine particles.

5. The chip of claim 1 for separating or aligning fine particles, wherein two or more inclined grooves are formed in a direction from the one end on which the inlet part is positioned to the end opposite the one end of the passage part, and an interval of the inclined grooves in a direction perpendicular to both side surfaces of the passage part is 0.5 to 10 times an average diameter of the fine particles.

6. The chip of claim 1 for separating or aligning fine particles, wherein two or more inclined grooves are formed in an inclined direction, and an interval between the inclined grooves in an inclined direction is at least 0.001 times an average diameter of the fine particles.

7. The chip of claim 1 for separating or aligning fine particles, wherein a height of the passage part on which the inclined groove is not formed is 0.5 to 10 times an average diameter of the fine particles.

8. The chip of claim 1 for separating or aligning fine particles, wherein the passage part is an integrated structure in fluid communication that connects the inlet part with the discharge part, and has a linear shape or a shape including one or more bending parts.

9. The chip of claim 1 for separating or aligning fine particles, wherein a cross sectional shape of the inclined groove is a convex polygonal shape, a concave polygonal shape, a circular shape, or an elliptical shape.

10. The chip of claim 1 for separating or aligning fine particles, wherein two or more inclined grooves are formed in a direction from the one end on which the inlet part is positioned to the end opposite the one end of the passage part, and the two or more inclined grooves are positioned on a straight line with centers thereof being in a direction perpendicular to the inclined side, or arranged in a position that is shifted toward the side surface where the fine particle discharge part is positioned.

11. The chip of claim 1 for separating or aligning fine particles, wherein the fine particles are cells.

12. The chip of claim 1 for separating or aligning fine particles, wherein the fine particles are leukocytes and the fluid is blood.

13. The chip of claim 1 for separating or aligning fine particles, wherein the fine particles are protein, or beads to which proteins or peptides are attached.

14. The chip of claim 13 for separating or aligning fine particles, wherein the fine particles are beads to which antibodies are attached.

15. A device for separating or aligning fine particles, comprising two or more chips of claim 1 for separating or aligning fine particles.

16. The device of claim 15 for separating or aligning fine particles, wherein the two or more chips for separating or aligning fine particles are arranged in parallel.

17. The device of claim 15 for separating or aligning fine particles, wherein the fine particles are cells.

18. The device of claim 15 for separating or aligning fine particles, wherein the fine particles are leukocytes.

19. The device of claim 15 for separating or aligning fine particles, wherein the fine particles are beads to which proteins or peptides are attached.

20. The device of claim 19 for separating or aligning fine particles, wherein the fine particles are beads to which antibodies are attached.

21. A method for separating or aligning fine particles, comprising:
   supplying a fluid including fine particles to an inlet part of the chip of claim 1 for separating or aligning the fine particles, or to an inlet of a device for separating or aligning the fine particles, wherein the device for separating or aligning fine particles includes two or more chips of claim 1; and
   collecting fine particles discharged from a fine particle discharge part of the chip for separating or aligning the fine particles or a fine particle discharge part of the device for separating or aligning the fine particles.

22. The method of claim 21 for separating or aligning fine particles, wherein the fine particles are cells.

23. The method of claim 21 for separating or aligning fine particles, wherein the fine particles are leukocytes and the fluid is blood.

24. The method of claim 23 for separating or aligning fine particles, wherein the blood is whole blood or blood which is diluted 1 to 20 times by volume with respect to whole blood.

25. The method of claim 21 for separating or aligning fine particles, wherein the fine particles are protein, or beads to which proteins or peptides are attached.

26. The method of claim 25 for separating or aligning fine particles, wherein the fine particles are beads to which antibodies are attached.

27. A kit for separating or aligning fine particles, comprising:
   the chip of claim 1 for separating or aligning the fine particles, or a device for separating or aligning the fine particles including two or more chips of claim 1; and
   a fluid supply part connected to an injection part of the chip for separating or aligning the fine particles, or to an injection part of the device for separating or aligning the fine particles.

28. The kit of claim 27 for separating or aligning fine particles, wherein the fluid supply part is selected from a group consisting of a syringe, a pipette, a piston pump, a syringe pump, a diaphragm pump, and a peristaltic pump.

* * * * *